United States Patent [19]

Kaster

[11] 4,441,215
[45] Apr. 10, 1984

[54] VASCULAR GRAFT

[76] Inventor: Robert L. Kaster, 2730 Vagabond La., Plymouth, Minn. 55447

[21] Appl. No.: 469,174

[22] Filed: Feb. 23, 1983

Related U.S. Application Data

[63] Continuation of Ser. No. 207,678, Nov. 17, 1980, abandoned.

[51] Int. Cl.³ .............................. A61F 1/00; A61F 1/24
[52] U.S. Cl. ...................................... 3/1.4; 128/334 R
[58] Field of Search ....................... 3/1.4, 1; 128/92 C, 128/334 R

[56] References Cited

U.S. PATENT DOCUMENTS

| 2,836,181 | 5/1958 | Tapp | 3/1.4 X |
|---|---|---|---|
| 3,095,017 | 6/1963 | Bleiler et al. | 3/1.4 X |
| 3,105,492 | 10/1963 | Jeckel | 3/1.4 X |
| 3,272,204 | 9/1966 | Artandi et al. | 3/1.4 X |
| 3,304,557 | 2/1967 | Polansky | 128/334 R |
| 3,317,924 | 5/1967 | Le Veen et al. | 3/1.4 |
| 3,463,158 | 8/1969 | Schmitt et al. | 128/334 R |
| 3,479,670 | 11/1969 | Medell | 128/334 R |
| 3,526,906 | 9/1970 | De Laszlo | 128/92 C X |
| 3,626,947 | 12/1971 | Sparks | 3/1.4 X |
| 3,710,777 | 1/1973 | Sparks | 3/1.4 X |
| 3,730,835 | 5/1973 | Leeper et al. | 3/1 X |
| 3,878,565 | 4/1975 | Sauvage | 3/1.4 X |
| 4,164,045 | 8/1979 | Bokros et al. | 3/1.4 |
| 4,193,138 | 3/1980 | Okita | 3/1.4 |

FOREIGN PATENT DOCUMENTS

| 2255743 | 5/1973 | Fed. Rep. of Germany | 3/1.4 |
|---|---|---|---|
| 2913510 | 10/1979 | Fed. Rep. of Germany | 3/1.4 |
| 628911 | 10/1978 | U.S.S.R. | 3/1.4 |

*Primary Examiner*—Ronald L. Frinks
*Attorney, Agent, or Firm*—Henderson & Sturm

[57] ABSTRACT

Vascular graft of synthetic material including a tubular member having a braided inner layer and a compliant outer covering layer where the braided layer includes a plurality of interwoven groups of filaments. The filaments can be constructed either of metal or of plastic. The compliant outer covering can be either a sleeve of processed biologic material such as collagen, processed plastic, liquid deposition of biologic material or plastic, or a combination of biologic and plastic materials. The inflow and outflow orifices of the tubular member are at an angle with respect to the longitudinal axis of the graft and are reinforced either by tacking of the filaments to adjoining filaments or by tacking an endless single-strand filament rim to the orifice in addition to reinforcement by the outer covering material. Also, the synthetic vascular graft can have an orifice braided and woven into the tubular member parallel to the longitudinal axis. Additionally, the synthetic vascular graft can have an increasing or decreasing taper.

9 Claims, 10 Drawing Figures

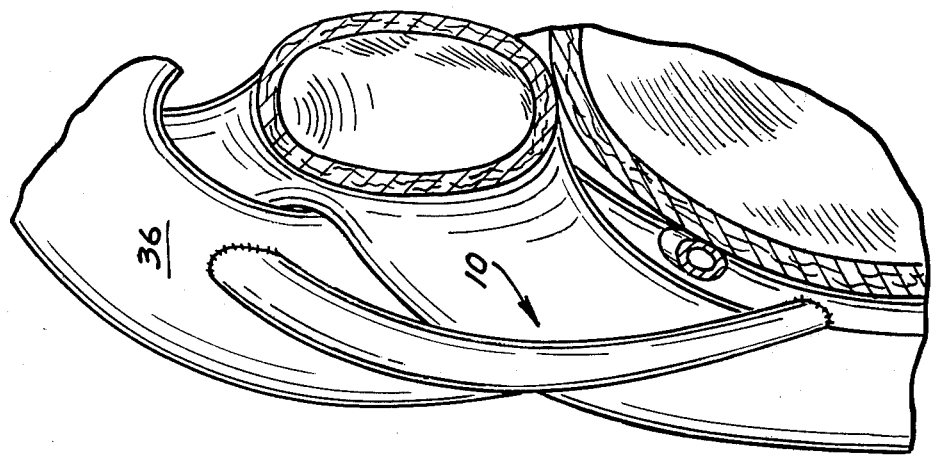
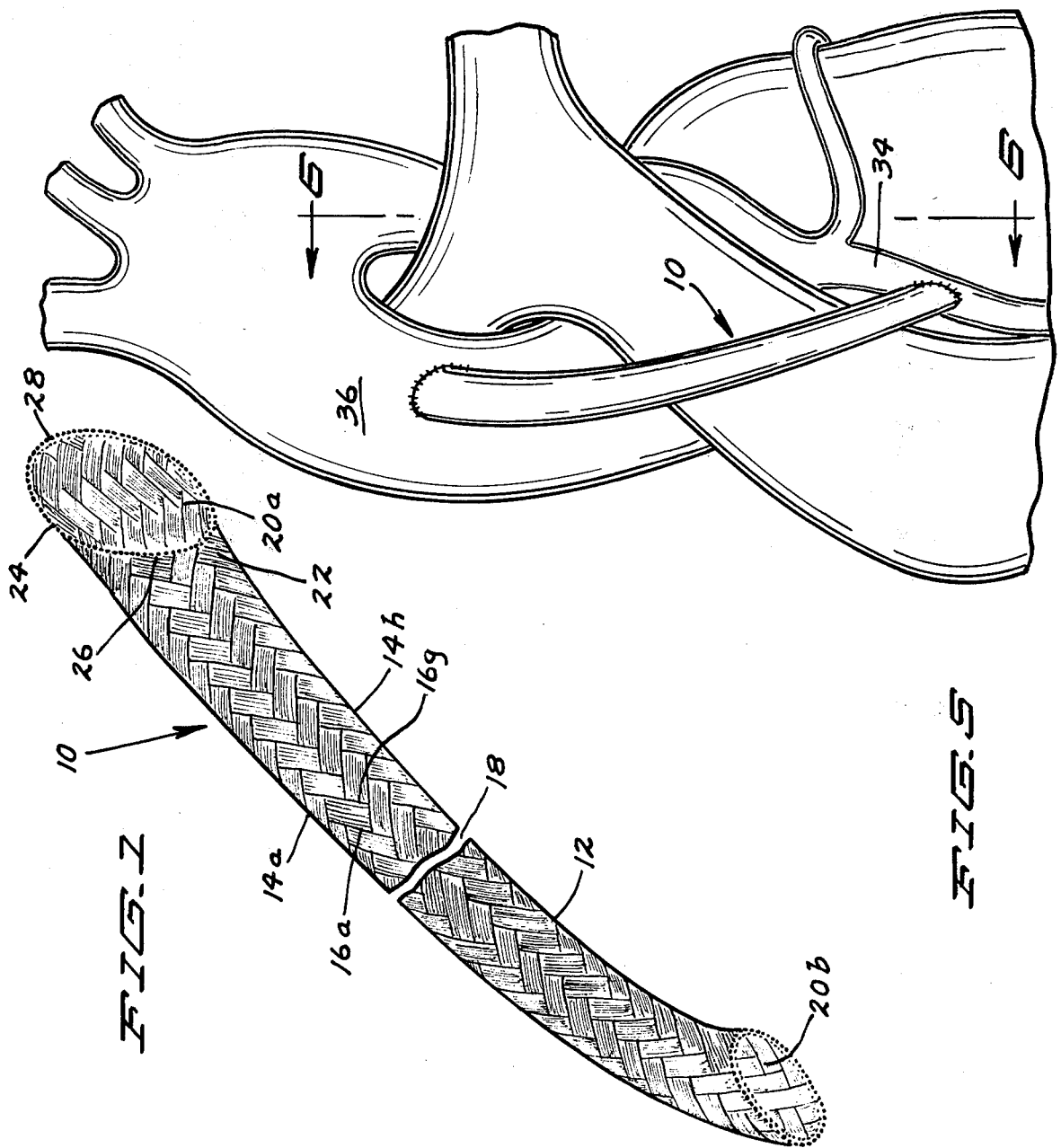

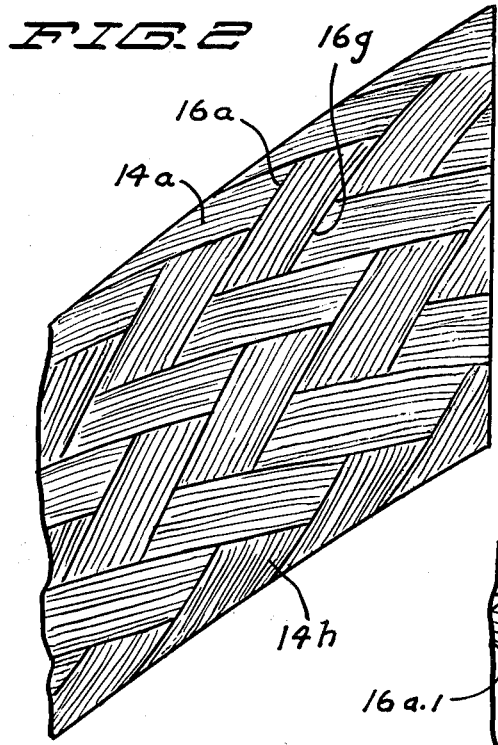
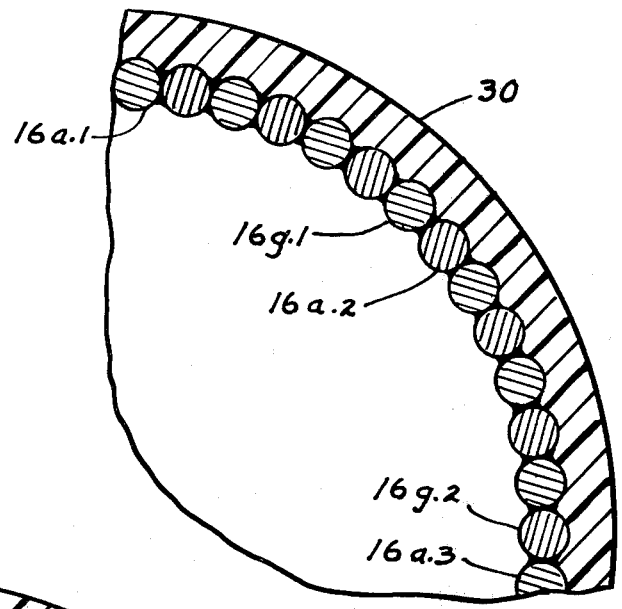
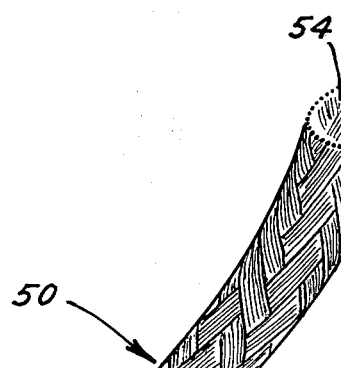
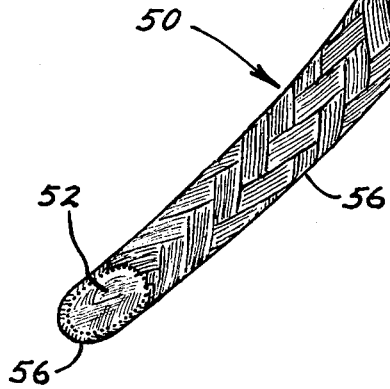
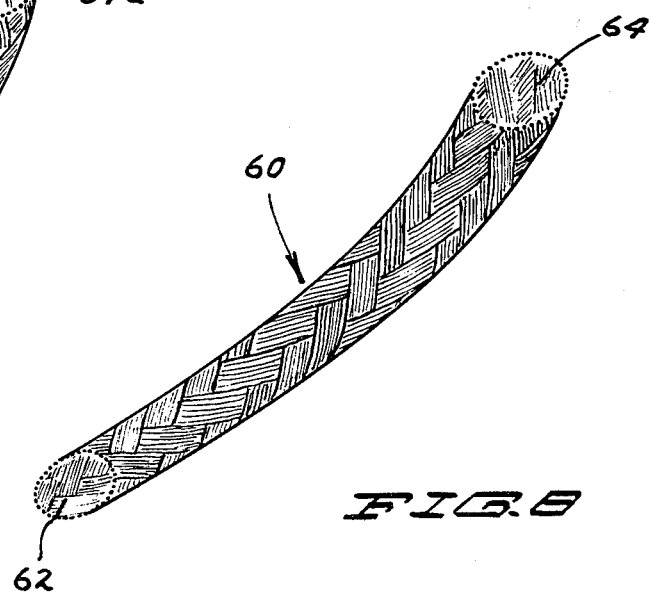

VASCULAR GRAFT

This application is a continuation of application Ser. No. 207,678, filed Nov. 17, 1980, now abandoned.

BACKGROUND OF THE INVENTION

1. Field of the Invention

The present invention pertains to a surgical prosthesis, and, more particularly, pertains to a synthetic vascular graft implantable prosthesis.

2. Description of the Prior Art

Diseases affecting the cardiovascular system are either congenital or acquired. An acquired cardiovascular disease can result from living habits, infections or injuries during embryonic life, or at any time following birth. Some diseases primarily affect the blood vessels; others only the heart itself.

Atherosclerosis is the major disease that affects the blood vessels. This disease may have its beginnings early in life and is first noted as a thickening of the arterial walls. This thickening is an accumulation of fat, fibrin, cellular debris and calcium. The resultant narrowing of the internal lumen of the vessel is called stenosis. Vessel stenosis impedes and reduces blood flow. Hypertension and dysfunction of the organ or area of the body that suffered the impaired blood flow can result.

As the buildup on the inner wall of a vessel thickens, the vessel wall loses the ability to expand and contract. Also, the vessel loses its viability and becomes weakened and susceptible to bulging, also known as aneurysm. In the presence of hypertension or elevated blood pressure, aneurysms will frequently dissect and ultimately rupture.

Small vessels, such as the arteries that supply blood to the heart, legs, intestines and other areas of the body, are particularly susceptible to atherosclerotic narrowing. The loss of blood supply to the leg or segment of the intestine may result in gangrene. Atherosclerotic narrowing of the coronary arteries impedes, limits and in some instances prevents blood flow to regional areas of the heart. Depending upon its severity and location within the coronary circulation, pain, cardiac dysfunction or death may result.

Vascular complications produced by a atherosclerosis, such as, stenosis, aneurysm, rupture and occlusion are, in the majority of cases, managed either medically or surgically. Control and elimination of hypertension is the more effective form of medical management. In cases in which atherosclerotic disease is advanced and the attendant complications jeopardize the health of the patient, surgical intervention is usually instituted.

Aneurysms and stenosis of major arteries are best corrected by a plastic reconstruction that does not require any synthetic graft or patch materials. However, if the disease is extensive and the vessel is no longer reliable, it is usually replaced by a graft. In such case, the involved vessel section is transected and removed and a synthetic patch, conduit or graft is sewn into place.

Medium sized arteries are operated on much the same as for large diameter vessels. But in some types of surgery where the replacement graft is of small diameter, handling and surgical placement of the graft is difficult. The internal diameter may be compromised due either to surgical technique or biological response. In some cases, the graft may become entirely occluded shortly after surgery.

Patients with coronary artery disease in which blood flow to part of the heart muscle has been compromised receive significant benefit from coronary artery bypass surgery. This type of surgery requires the use of grafts of small diameter. These grafts, the majority of which are biologic, have certain inherent problems. Synthetic grafts are only used on infrequent occasions because they are more problematical than biologic grafts. It is the purpose of this invention to obviate and eliminate certain of the more significant problems associated with the surgical procedure of coronary artery bypass and the implanted grafts following surgery.

In a patient who undergoes coronary artery bypass surgery, a non-critical artery or vein of small diameter is harvested from elsewhere in the body and sewn into place in a manner that reestablishes flow to the area of the heart that earlier lost its blood supply because of atherosclerotic blockage and is referred to as an autograft. When no suitable artery or vein can be harvested, an allograft or xenograft vessel may be employed. However, experience with these latter two graft types is limited because of unsatisfactory results. A synthetic graft is an alternative to an allograft or a xenograft. But, like the allograft and xenograft, the synthetic counterpart does not produce acceptable results.

Although the heart benefits immediately from the reestablished blood supply of the bypass, there is no assurance the graft will function trouble free indefinitely. The autograft, because it is harvested from the patient, who in all probability is being operated on for atherosclerotic artery disease, is highly susceptible to atherosclerosis following surgery. Most harvested veins used in coronary artery bypass surgery exhibit some degree of atherosclerosis.

The long vein in the leg called the saphenous vein is the most commonly harvested vein for use as a vein bypass graft, (autograft), in coronary artery surgery. Most saphenous vein bypass grafts, in time, exhibit a narrowing of the lumen unlike that of atherosclerosis. It is believed this is a pathologic response of the vein because it is of different cellular construction and composition than an artery—a condition for which it is not best suited. Harvesting a saphenous vein autograft is a tedious surgical task and not always rewarded with the best quality graft. Also, removal of the saphenous vein disrupts the natural venous blood return from the leg and is not therapeutically recommended except for medical reasons such as in a patient with advanced venous disease such as varicose veins. Finally, harvesting an autograft in the operating rooms requires additional surgical time and expense.

These noted limitations of the saphenous vein autograft have generated interest in a synthetic graft for coronary artery bypass. Clinical experience with small diameter synthetic grafts for coronary artery bypass dates back to the mid 1970's. Teflon and Dacron fibers are the most commonly employed materials for synthetic grafts. However, despite the different methods and techniques of graft construction such as woven or knit, velour, texturized or non-texturized, tight or loose, fine or coarse, expanded or non-expanded, variations in fiber diameter and wall thickness, etc., no graft of small lumen diameter has shown a resistance to blockage by thrombus. However, synthetic grafts of large diameter consistently remain patent and trouble-free for extended periods of many years. This finding is consistently repeated where a small-diameter synthetic graft is used to bypass a blocked coronary artery. Therefore, despite their inherent limitations, autografts employing the saphenous vein remain the graft of choice for coronary artery bypass surgery.

The coronary artery circulation begins with the right and left coronary arteries. These two arteries in turn give rise to an extensive coronary circulation. Generally, atherosclerosis affects the larger coronary arteries. Therefore, a patient being operated upon for coronary artery disease will receive two or more vein grafts of various length and diameter depending upon the location of the blockage and the usable harvested saphenous vein.

Even though coronary artery bypass surgery is widely practiced and has become a routine procedure in hospitals throughout the world, it is not without certain operative limitations that would best be avoided. Sewing the graft to the host vessel, known as an anastomosis, requires delicate surgical techniques to accomplish the best possible result. There are several complications to be avoided when anastomosing a vessel and graft together. It is important that the junction between the host tissue and graft be a uniform transition without narrowing and regional irregularities such as protuberances that bulge into the lumen or sinuses that extend outward of the lumen. A narrowing at the site of anastomosis reduces blood flow. Protuberances into the lumen obstruct blood flow and may produce turbulence. Lastly, blood that stagnates in a sinus or cavity tends to clot and obstruct the vessel lumen and subsequently the blood flow. All these characteristics diminish the effectiveness and patency of the graft.

Summarizing, the limitations associated with the autograft as applied in coronary artery bypass surgery are: tedious surgical task to harvest, physically imperfect and irregular lumen, tedious surgical task to anastomose to host vessel, physically imperfect anastomosis of irregular and unsmooth transition between graft and vessel, functional narrowing of vein graft lumen during early postoperative period, and occlusion of the autograft due to thrombosis and/or continuance of the pre-existing atherosclerotic process.

The synthetic vascular graft of the present invention overcomes the deficiencies of the prior art and provides a synthetic vascular graft that significantly improves the results of coronary artery bypass surgery. This synthetic vascular graft eliminates the time of the tedious surgical task of harvesting a saphenous vein. The lumen of the synthetic vascular graft is not comprised of natural anatomical irregularities as those that are common to the prior art vein grafts. The synthetic vascular graft minimizes the task of forming anastomotic connections to the ascending aorta at the proximal end and the coronary artery distally. The synthetic vascular graft also does not exhibit narrowing associated with implants of the saphenous vein grafts and will not exhibit occlusion and blockage due to atherosclerosis.

SUMMARY OF THE INVENTION

The general purpose of the present invention is a synthetic vascular graft for implantation in the human body, and particularly for use in coronary artery bypass surgery. The synthetic vascular graft includes a multifilament braided conduit overlaid with a compliant flexible covering in a single surgical prosthesis.

According to one embodiment of the present invention, there is provided a vascular graft including a tubular member having a braided inner layer, the braided inner layer including a plurality of interwoven groups of filaments where each filament can be of metal or plastic composition, proximal and distal orifices at respective ends of the tubular member, and a compliant outer covering which can be either a sleeve of processed biologic material such as collagen, processed plastic or liquid deposition of biologic material or plastic, or a combination of biologic and plastic materials. The proximal and distal orifices can be at an angle with respect to the longitudinal axis of the tubular member as warranted by widely variant vascular anatomy.

A significant aspect and feature of the present invention is a cost effective synthetic vascular graft providing for safety of surgical implantation and efficacy in vivo. While the proximal and distal anastomosis of the graft are hand stitched at predetermined locations, minimal time is required as the inflow and outflow orifices are defined providing for accurate placement of the stitches about the orifices.

Another significant aspect and feature of the present invention is a synthetic vascular graft which requires a least amount of surgical handling and which can be chosen to conform to the contour of the heart. The orifices of the synthetic vascular graft are readily discernible throughout the anastomotic stitching process and the lay of the interwoven braid prohibits inadvertent twisting during or after implant.

A further significant aspect and feature of the present invention is a synthetic vascular graft that is available in a range of lumen sizes and lengths. This is particularly beneficial because the surgeon can request the correct size graft in each instance from an inventory of sizes stocked in sterile surgical supplies. The patient is the ultimate beneficiary, having received the correct size graft to suit his particular coronary circulatory requirements.

Having thus described one embodiment of the present invention, it is a principal object hereof to provide a synthetic vascular graft as an implantable prosthesis.

An object of the present invention is a synthetic vascular graft that provides lumen patency at surgical implantation. The interwoven braid of the synthetic vascular graft forms an interwoven spiral that prohibits crushing of the lumen by external pressure, localized projections or short radius turns. The synthetic vascular graft does not undergo chemical or physical change, especially with respect to the lumen. The braided interwoven groups are of a filament size withstanding normal compression. Also, the synthetic vascular graft functions free of complications attendant to atherosclerosis.

Another object of the present invention is a synthetic vascular graft that can be stocked as surgical supplies in different sizes and configurations with regard to lengths, diameters, and orifice angles.

A futher object of the present invention is that the synthetic vascular graft can include an outer covering of a biologic compatible material or materials including a processed biologic material.

An additional object of the present invention is a compliant outer covering that insures blood flow through the graft with no passthrough of blood through the porosity of the outer covering and that provides biocompatibility.

BRIEF DESCRIPTION OF THE DRAWINGS

Other objects and many of the attendant advantages of this invention will be readily appreciated as the same becomes better understood by reference to the following detailed description when considered in connection with the accompanying drawings, in which like reference numerals designate like parts throughout the figures thereof and wherein:

FIG. 1 illustrates a plan view of a synthetic vascular graft, the present invention;

FIG. 2 illustrates a section of the surface of the synthetic vascular graft;

FIG. 3 illustrates a partial cross-section of the synthetic vascular graft with a chemical processed compliant covering;

FIG. 4 illustrates a partial cross-section of the synthetic vascular graft with a compliant covering;

FIG. 5 illustrates a plan view of the synthetic vascular graft implanted between the wall of the ascending aorta and a coronary artery of the heart;

FIG. 6 illustrates a sectional view taken along line 6—6 of FIG. 5;

FIG. 7 illustrates another embodiment of a synthetic vascular graft; and,

FIG. 8 illustrates an additional embodiment of a synthetic vascular graft.

DESCRIPTION OF EMBODIMENTS

Figure 1A:
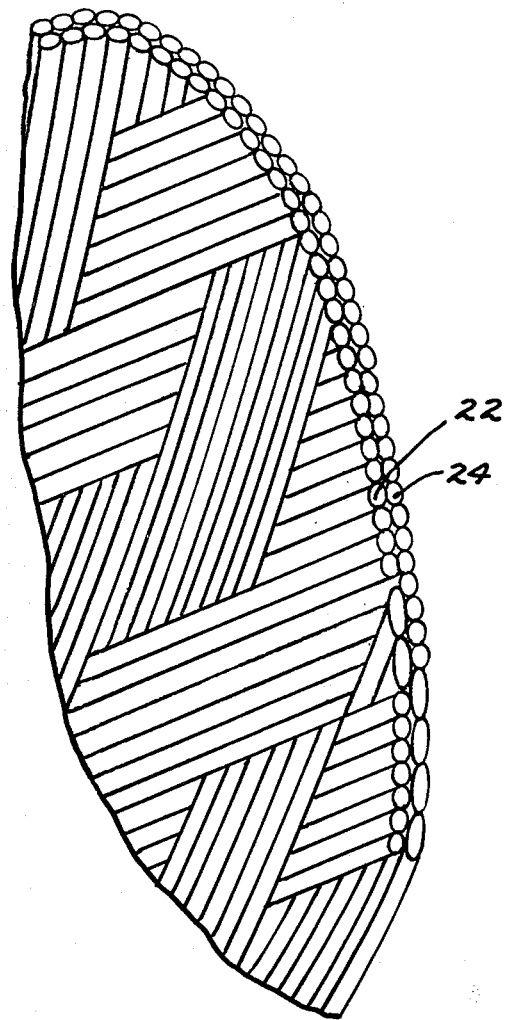
FIG. 1A illustrates a partial section of an inflow orifice.

FIG. 1, which illustrates a synthetic vascular graft 10 of the present invention, shows a braided layer 12 of sixteen interwoven groups 14a-14p, 14a-14h illustrated including filaments 16a-16g for each one of the groups. The groups 14i-14p are on the opposing side not visible in the figure. The braided layer 12, by way of example and for purposes of illustration only and not to be construed as limiting of the present invention, can include sixteen interwoven groups of filaments with seven filaments for each group. A filament, by way of example and for purposes of illustration only, is in the range of 0.1 mm in diameter and lies in a side-by-side relationship with each of the other filaments. The sixteen groups are interwoven thereby forming a tubular member 18 of the synthetic vascular graft 10. The tubular member 18 is both pliable and flexible. Inflow orifice 20a at the proximal end and outflow orifice 20b at the distal end are disposed in the ends of the tubular member 18 of the synthetic vascular graft 10, and can be reinforced for sustaining the forces of stitching during surgery, as later described. The inflow orifice 20a at the proximal end includes a circumferential rim which forms an angle in the range of 15°-90° with the central longitudinal axis of the vascular graft 10, and in this illustration 60°. The particular angle is dependent on the physical and surgical requirements of the vascular graft 10. The circumferential rim of the inflow orifice 20a is substantially circular for facilitating anastomotic suturing to the ascending aorta, but can also assume an oval or elliptical shape. The cross-section of the vascular graft is illustrated as being circular, but can also be elliptical, and is not to be construed as limiting of the present invention.

The outflow orifice 20b at the distal end includes a circumferential rim which assumes substantially the same shape and configuration as the inflow orifice 20a, and which forms an angle in the range of 20°-90° with the central longitudinal axis of the vascular graft 10, and in this illustration 35°, and which can assume a circular or oval or elliptical shape.

Figure 1B:
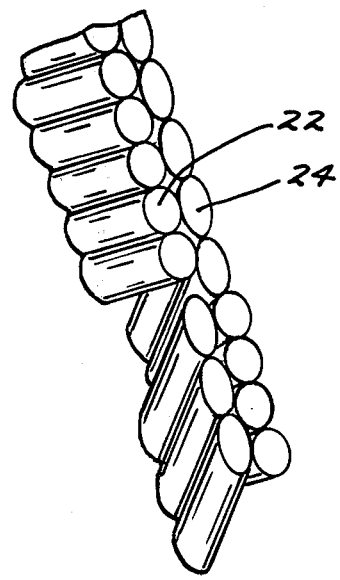
FIG. 1B illustrates an enlarged partial section of FIG. 1A.

One form of reinforcing the orifices 20a and 20b is tack welding the filament ends to adjacent filament ends or to the outer filament which passes through parallel to the plane of the orifice. Depending upon the particular angle of the orifice, the terminated filament strands at the orifice can appear as either circular dots 22 or elliptical dots 24, or as a filament strand 26 which passes substantially parallel and adjacent to the plane of the orifice. Depending upon the particular angle of the orifice, a plurality of groups 28 of filaments either parallel or offset with respect to each position about the orifices, as illustrated at orifices 20a and 20b, and as also illustrated in FIGS. 1A and 1B. The terminated filament ends are tack welded to each other and filament ends are welded to filament strands parallel to the orifice plane thereby forming a substantially pliable and reinforced rim suitable for suturing during implantation. The tack welds can also follow a sinusoidal, sawtooth or squarewave pattern substantially 3 mm to 6 mm peak to peak substantially adjacent to the rim thereby yielding a pliable, resilient and reinforced rim. During the tack welding or other suitable fastening process, some of the tacks of strands to adjacent strands can be omitted as predetermined.

The length of the vascular graft 10 will be in the range of 7 cm-25 cm and have a diameter in the range of 3 mm-7 mm. The specific synthetic vascular graft 10 selected during surgery is dependent on the length, diameter of the lumen, and angles of the proximal and distal orifices. During surgery, surgeons will have a readily available quantity of different vascular grafts from which to select. Compliant flexible covering engages over the external surface of the synthetic vascular graft 10 for prohibiting passage of blood through the graft. The covering can be either processed biologic material or a chemical curing synthetic material 30 that adheres to the braided member 12 as illustrated in FIG. 3, or tight-fitting knitted, woven, or expanded fabric sleeve 32 over the braided member 12 as illustrated in FIG. 4, both as later discussed in detail; or a combination of materials such as a fabric sleeve, a plastic sleeve covering the fabric sleeve, and a covering of processed biologic material over the plastic sleeve.

The individual filaments utilized in the braided tubular member 18 of interwoven groups of the synthetic vascular graft 10 can be metal such as titanium, tantalum, nickel, or stainless steel such as Haynes-25, Stellite-21, 304 or 316; or, the individual filaments can be of monofilament polypropylene or polyethylene such as Dacron, Prolene or Teflon. The filaments can also be a processed biologic material, such as collagen. The filaments can also be coated with Biolite which is a processed carbon material or other suitable material.

FIG. 1A, which illustrates a partial section of the inflow orifice 20a, shows the offset terminated filament ends where the filaments are substantially parallel to each other in two substantially parallel and offset interwoven groups of filaments. The offset filament ends include terminated ends assuming the geometrical configuration of either circular dots 22 or elliptical dots 24 as previously described in FIG. 1. The particular geometrical shape is dependent upon the existing angle of each of the filament ends and the inclination of the plane of the orifice to the central axis of the lumen. FIG. 1A is one of the cases of terminated filament ends where the other cases include single terminated filament ends or filament strands passing parallel to the orifices.

FIG. 1B, which illustrates an enlarged section of FIG. 1A, again shows the circular dots 22 and elliptical dots 24 which are adjacent to each other at the inflow orifice 20a as previously described above.

FIG. 2, which illustrates an enlarged section of the plan view of the synthetic vascular graft 10 of FIG. 1 shows the pluralities of groups 14 of filaments 16a–16g where each group includes seven filaments by way of example and for purposes of illustration only. Each group 14 of filaments is interwoven at an angle with respect to each of the other groups 14.

FIG. 3, which illustrates a partial cross-section of the synthetic vascular graft 10, shows a plastic type material such as latex-rubber, silicone-rubber, Avcothane, Biomer, polyurethane, or other similar chemical curing plastic material 30 and including processed biologic material such as bovine collagen. The orifices 20a and 20b can be further reinforced by an additional deposition of the plastic or biologic material. The figure also illustrates a configuration where the terminated ends of the filaments assume the geometrical shape of dots across the cross-section. The figure further illustrates the tacking of each of the terminated filaments together, and material which partially fills in between each of the filaments.

FIG. 4, which illustrates a partial cross-section portion of the synthetic vascular graft, shows an outer covering of a fabric sleeve which can be constructed of a woven, knitted or expanded Teflon, woven or velour Dacron, or other woven plastic or derivative material. The inner diameter of the sleeve 32 lies across each of the filaments. Again, tack welded material, preferably the filament material, fills in between each of the filaments. Any other suitable securing processes can be utilized in lieu of the tack welding.

The outer coverings of FIGS. 3 and 4 can include a single compliant material as previously set forth or a combination of materials such as a first material overlying a second material. Such an example would be a first outer covering of compliant material such as plastic and then a second outer covering of compliant material such as processed biologic material such as bovine collagen. It is also understood that there can be any number of outer coverings over the braided interwoven groups.

MODE OF OPERATION

Synthetic vascular graft or grafts which are to be implanted are predetermined by the location of the coronary artery blockage and the surgical accessibility. The size of patent downstream coronary arteries that a graft can be anastomosed to determines the number and size of bypass synthetic vascular grafts that need to be implanted for the best surgical result. In most cases, the surgeon will implant three or more bypass grafts in each patient who undergoes coronary artery bypass surgery. For purposes of illustration and example only, the description for the mode of operation is limited and directed to an implant of one synthetic vascular graft, and is not to be construed as limiting of the present invention, as the description can be extended to more than one bypass synthetic vascular graft implant as required.

FIGS. 5 and 6 illustrate a plan and sectional view respectively of an implanted synthetic vascular graft, and are applicable to the description following for a suggested procedure for the implantation of the synthetic Vascular graft 10.

The coronary artery downstream from the blockage is exposed and found to be of sufficient size that is anatomically compatible with a synthetic vascular graft having a 4 mm internal diameter, by way of example and for purposes of illustration. The distance is measured between the proximal anastomotic site on the wall of the ascending aorta and the distal anastomotic site of the surgically exposed coronary artery. An accurate measurement of this distance also takes into account both the curvature of the heart and the range of motion of the heart that results from the heart beat after the chest is closed.

The patient is placed on total cardiopulmonary bypass, the heart is arrested, and the distal coronary artery opened and prepared for the anastomotic connection. The 4 mm size graft is confirmed and a graft of a predetermined length is selected with predetermined orifice angles corresponding to that of the aorta and artery of the heart. To anastomose the synthetic vascular graft to the aorta proximally and the coronary artery distally requires modification of previously known surgical techniques used for a saphenous vein graft. The differences between these two grafts is appreciated to avoid surgical difficulties in that the prior art saphenous vein graft is markedly flexible and easily tailored to the correct length while the synthetic vascular graft 10 of the present invention is less flexible and not readily elongated or tailored to a shorter length. Therefore, it is important to size the vessels and graft correctly, measure the required length accurately, and select the predetermined correct sized synthetic vascular graft 10 from surgical supply as required.

First, the distal anastomosis is preformed but only partially sewn to allow for venting of air from the graft. Next, the graft is positioned on the surface of the heart as illustrated in FIGS. 5 and 6. The inflow orifice of the synthetic vascular graft 10 is orientated relative to the ascending aorta for verifying the preselected site of the proximal anastomosis. Any adjustments in location are easily implemented because the hole in the ascending aorta has not yet been made.

Second, depending upon the individual surgeon's technique and personal preference, a 4 mm to 5 mm round hole, for purposes of this example, is made at the selected site in the wall of the ascending aorta using an instrument especially designed for the procedure. The proximal end of the graft is stitched to the wall of the aorta taking care to superimpose the inflow orifice directly over the hole in the aorta. The stitching technique should not vary significantly from the techniques usually utilized for the proximal anastomosis of a saphenous vein graft.

Blood from the aorta is then allowed to fill the synthetic vascular graft 10 for flushing of air through the functionally incompetent distal anastomosis. After sufficient flushing, the distal anastomosis is finally made competent. The flared circumferential rims at both orifices act to conform with surrounding tissue, therefore providing for a competent and leak-proof anastomotic junction.

FIG. 5 illustrates a completed anastomosis of the synthetic vascular graft 10 between the aorta 36 and coronary artery 34.

FIG. 6 illustrates the angular relationship of the orifices of the synthetic vascular graft 10 to the aorta and coronary artery 34.

ALTERNATIVE EMBODIMENT

Synthetic Vascular Graft with side Positioned Orifice

FIG. 7, which illustrates a plan view of an alternative embodiment of a synthetic vascular graft 50 including a side positioned distal orifice 52, shows the interwoven groups of filaments as previously described, the inflow orifice 54 at the proximal end, and the outflow orifice 52 which is positioned at the distal end of the graft and which assumes a predetermined geometrical shape. In this particular embodiment, the outflow orifice 52 is illustrated as elliptical, but can also assume a circular, oval or other geometrical form. During the weaving process of the groups of filaments, the outflow orifice 52 is woven into the side of the tubular member 56. The outflow orifice can be further reinforced with compliant outer covering material or by a reinforcing rim about the hole as previously described for FIG. 1. The inflow orifice 54 illustrates a rim 54a of filament material reinforcing the orifice and to which all terminated filament strands are tacked either through welding or suitable processes, and terminated filament ends are tacked to adjacent strands passing parallel to the rim as also previously described in FIG. 1.

ALTERNATIVE EMBODIMENT

Synthetic Vascular Graft with Tapered Lumen

FIG. 8, which illustrates a plan view of an alternative embodiment of a synthetic vascular graft 60, shows interwoven groups of filaments increasing in numbers of filaments and groups proportionately from an outflow orifice 62 at a distal end to an inflow orifice 64 at a proximal end. The lumen of the graft 60 tapers uniformly over the longitudinal length, and the change in cross-sectional area is two-thirds from the inflow orifice to the outflow orifice. The graft 60 can also be made with a taper from one end to the other end without varying the number of filaments in each group or adding groups of filaments depending on the taper of the graft 60.

Various modifications can be made to the synthetic vascular graft of the present invention without departing from the apparent scope thereof. The materials of the synthetic vascular graft can be selected from the materials previously delineated or any other suitable material can be substituted. While the terms braided and interwoven are utilized in describing the braided layer of interwoven groups of filaments, any other type of braiding of interwoven groups can be utilized, especially different configurations of overlaying the filaments which is construed as being within the claims of this disclosure.

Having thus described the present invention, what is claimed is:

1. Non-corrugated vascular graft implantable prosthesis comprising:
   a. tubular member including an inner layer comprising a plurality of filament arrays, each said filament array including at least three filaments that are disposed as a group substantially parallel and coplanar with respect to one another, and a compliant outer covering of material, said plurality of filament arrays being braided together to form a non-corrugated inner braided tube;
   b. inflow and outflow orifices at each end of said tubular member; and,
   c. means securing said filaments at said orifices to adjacent filaments and filament ends whereby said tubular member provides a flexible vascular graft thereby providing for passage of blood through said vascular graft.

2. Vascular graft of claim 1 wherein said inflow orifice forms an angle with a longitudinal axis of said tubular member in the range of 15°–90°.

3. Vascular graft of claim 1 wherein said tubular member is flared from one of said orifices to said other orifice.

4. Vascular graft of claim 3 wherein said flare increases from said outflow to said inflow orifice.

5. Vascular graft of claim 4 wherein cross-sectional area of said flare increases by substantially one-third.

6. Vascular graft of claim 1 comprising one or more filaments interwovenly encircling at least one of said orifices.

7. Vascular graft of claim 6 wherein terminated filaments and parallel filaments are affixed to said interwoven filaments.

8. Vascular graft of claim 1 comprising a second outer covering over said compliant outer covering.

9. In a non-corrugated vascular graft implantable prosthesis of the type having an inner braided tube disposed within a compliant outer covering, an improvement comprising the provision of a plurality of filament arrays, each said filament array including at least three filaments that are disposed as a group substantially parallel and coplanar with respect to one another, said plurality of filament arrays being braided together to form said inner braided tube in a non-corrugated manner.

* * * * *